(12) United States Patent
Freitas et al.

(10) Patent No.: US 6,415,789 B1
(45) Date of Patent: Jul. 9, 2002

(54) SWIVEL STRUCTURE

(75) Inventors: Michael W. Freitas, North Richland Hills, TX (US); Sean P. Hanson, Murray, UT (US)

(73) Assignee: Sorenson Critical Care, Inc., Murray, UT (US)

( * ) Notice: Subject to any disclaimer, the term of this patent is extended or adjusted under 35 U.S.C. 154(b) by 239 days.

(21) Appl. No.: 08/794,337

(22) Filed: Feb. 3, 1997

(51) Int. Cl.$^7$ .................................................. A62B 9/04
(52) U.S. Cl. ........................... 128/202.27; 128/207.14; 128/912
(58) Field of Search ................... 128/202.27, 203.24, 128/205.19, 206.29, 207.14, 911, 912; 285/921, 331, 272; 604/905

(56) References Cited

U.S. PATENT DOCUMENTS

| | | | |
|---|---|---|---|
| 4,508,367 A | * 4/1985 | Oreopoulos et al. | 604/905 |
| 4,521,038 A | * 6/1985 | Cerny | 128/912 |
| 4,557,261 A | * 12/1985 | Rügheimer | 128/912 |
| 4,679,827 A | * 7/1987 | Law | 285/331 |
| 4,919,127 A | * 4/1990 | Pell | 128/912 |
| 5,071,413 A | * 12/1991 | Utterberg | 604/905 |
| 5,220,916 A | * 6/1993 | Russo | 128/912 |
| 5,285,776 A | * 2/1994 | Bertram | 128/912 |
| 5,357,946 A | * 10/1994 | Kee et al. | 128/912 |
| 5,579,762 A | * 12/1996 | Lee | 128/912 |

* cited by examiner

Primary Examiner—John G. Weiss
Assistant Examiner—V. Srivastava
(74) Attorney, Agent, or Firm—Traskbritt

(57) ABSTRACT

A connector for openly connecting conduits includes male and female parts adapted to couple by plug fit connection and structured to permit relative rotational displacement in coupled condition.

11 Claims, 1 Drawing Sheet

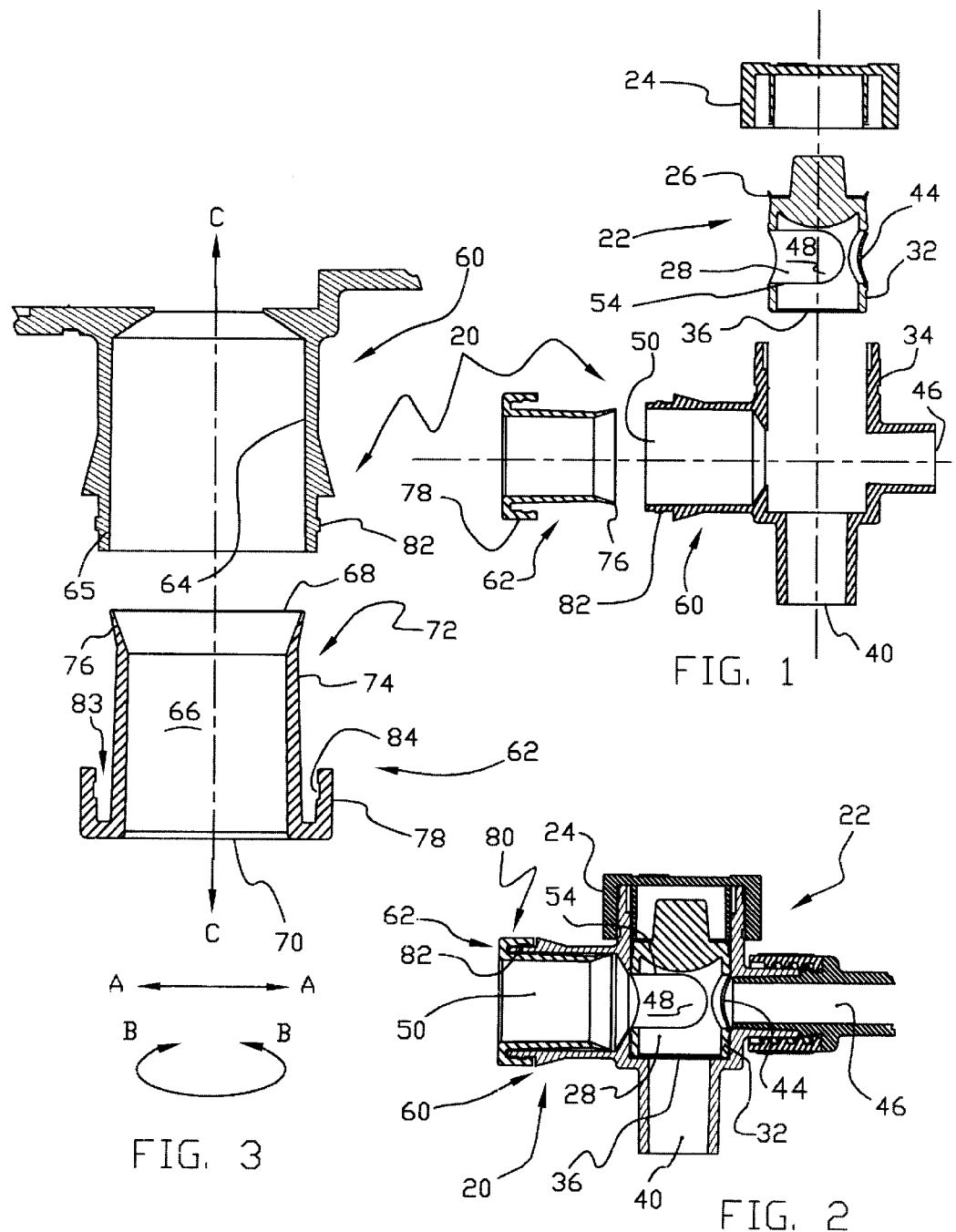

SWIVEL STRUCTURE

BACKGROUND OF THE INVENTION

1. Field

This invention relates generally to tubular connectors. It is specifically directed to rotatable joint structures which provide a sealed passageway between the interiors of discrete components of a fluid-containing assembly. A representative such joint structure is embodied as a connector at the interface between an intubation patient fixture and an endotracheal catheter assembly.

2. State of the Art

There are a variety of circumstances in which it is necessary or desirable to provide a flow or other travel path through the interiors of adjacent components of a fluid-containing assembly of discrete components. When the individual components of such an assembly are subjected to mechanical forces tending to rotate one component with respect to another, it is often essential to provide that travel path through a joint structure which permits rotating or swiveling movement. In many cases, the cost constraints imposed by a given application impose a practical limitation on the permissible expense of any joint structure included within the system.

As an example, closed systems for endotracheal suctioning and ventilating typically include a manifold enabling introduction of ventilating gases and intermittent exhalation of patient breath simultaneously with insertion and operation of a tracheal suctioning catheter. The manifold structure typically includes multiple ports, usually the open ends of respective conduits extending from a common chamber. One such port is interfaced to a patient through a patient connection device. The suction catheter is often included within an assembly which is connectable to a second port of the manifold. The catheter assembly conventionally includes a collapsible plastic envelope positioned entirely to surround the catheter. A practitioner manually externally collapses the envelope onto the external surface of the catheter, and advances the catheter through the manifold into an access tube connected to a patient, retracting the catheter in a similar fashion following the aspiration procedure.

Manipulations, or other disturbances, of the catheter assembly tend to cause irritation to the patient, and to impose strain on connection points within the assembly. These problems are alleviated to a considerable extent by the provision of a swivel capability (rotation about the longitudinal axis of the connection port) at the patient interface. Unfortunately, the provision of such a capability has heretofore involved the incorporation of swivel elements which are inordinately expensive and/or which provide an unreliable seal for the system.

Material prior art structures and methods are described, among other places, in U.S. Pat. No. 4,569,344 to Palmer. The '344 patent illustrates an aspirating/ventilating system of the type referred to in this disclosure. The illustrated system typifies the problem addressed by the present invention.

There remains a need for an inexpensive, yet reliable, connection structure capable of providing a sealed passageway through a rotating or swiveling joint.

SUMMARY OF THE INVENTION

The present invention provides an improved swivel connection apparatus which is generally useful for providing a gas-tight passageway between the interiors of discrete components of a fluid delivery system. The apparatus is structured and arranged to permit connection between tubular elements or conduits associated with such components. It is uniquely useful for connecting tubular elements of medical apparatus and the like. Accordingly, it is described in this disclosure with particular reference to one such application; endotracheal ventilating and aspirating assemblies. It is not thereby intended to suggest that the applicability of this improvement is limited to the medical field or to the scale appropriate for medical intubation devices. The connector of this invention is generally useful in connection with low pressure systems requiring an inexpensive joint connection. While the invention may be embodied in robust versions suitable for use in high pressure and/or large scale applications, alternative structures are available for such applications, and the benefits of this invention are correspondingly less apparent.

The invention may be embodied as an element of a manifold, typically a multi-functional manifold positioned at the distal end of a catheter assembly. A catheter tube is slidable lengthwise through a passageway between proximal and distal sides of the manifold. The manifold preferably includes a conduit at its distal side for attachment to (and communication with) an indwelling intubation device, such as a tracheal tube, endotracheal tube or nasopharyngeal tube. The manifold also preferably includes a ventilating structure extending radially from (and in fluid communication with) the passageway. The ventilating structure constitutes means for selectively introducing ambient air, oxygenated air and other therapeutic gases into the respiratory system of the patient. Other conduits may also be provided for the introduction of therapeutic and diagnostic implements and for the introduction of other suitable gases and lavage solutions to the respiratory system.

The manifold may be structured and arranged to enable simultaneous patient ventilation and protected tracheal suctioning. A suctioning catheter may be coupled at its proximal end to a suctioning valve. The distal end of the catheter may then be fed through a conduit at the proximal side of the manifold for reciprocal movement through the intubation device. The catheter is often provided in an assembly, whereby it is enveloped by a sterility-enhancing protective barrier, which is coupled to the proximal side of the manifold.

In use, the manifold assembly is interposed between an indwelling tube at the distal end of the manifold and a ventilating circuit. These junctions preferably embody a swivel configuration to permit left or right bedside placement of the ventilation circuitry, and free rotation of the ventilation circuit with patient head movement to reduce the risk of extubation. The present invention provides a particularly advantageous such connection.

The connector of this invention comprises a pair of cooperating parts. The first such part typically comprises a structural element carried by a system component, such as the manifold of an endotracheal ventilation system. This structural element may take a variety of forms, but in any case presents an approximately cylindrical interior surface, constituting the female portion of the connector.

The second part of the connector usually has a hollow interior between first and second open ends. Each such end is structured and arranged to couple with respective discrete system components. The first open end of the second part constitutes the male portion of the connector. It includes an outer surface configured to register, in sliding seal relation, with the female portion of the connector. This outer surface is thus approximately cylindrical, and is sized appropriately for insertion within the female portion. The distal end segment of the hollow cylinder (the male portion) is flared to an enlarged diameter so that it effects a self-biased engagement with the interior surface of the female portion across a relatively small surface area. In this fashion, an effective gas seal is maintained by the natural hoop strength of the flared end, with only a minor amount of frictional resistance against rotation of the male portion of the connector within the female portion of the connector. The flared segment is usually of reduced wall thickness and somewhat more flexible than the remainder of the male portion. The seal created by mating of the female and male portions is effective when the pressure within the hollow center of the connector is either positive or negative with respect to ambient conditions, within the practical range normally encountered in medical applications.

The second open end of the second part of the connector is structured and arranged for coupling to a second system component. For example, a tube may be press fit into an entry port opening into the second end to effect a mechanical connection. Rotation of the tube then effects equivalent rotation of the male portion within the female portion of the connector, thereby avoiding strain in the joint between the system components. A terminal segment of the second end may further be structured cooperatively to form a journal bearing connection with structure associated with the first part of the connector. In this fashion, the first and second parts are supported against radial displacement or twist, which could interfere with smooth rotational displacement of these parts with respect to each other.

An alternative embodiment substitutes, or includes as an interchangeable element, a second part with a closure of the hollow interior. This closure may be at the first end or otherwise constitute an occlusion of the open interior spaced from the flared distal end. This modification may serve as a plug in appropriate circumstances.

Thus, according to this invention, a connector for openly connecting conduits includes approximately cylindrical male and female parts adapted to couple ideally by a plug fit, (such as a snap fit or press fit) connection, and those parts are structured to permit relative rotational displacement while they are in coupled condition. One part, usually, the female part, may be constructed of any rigid material. The other, usually the male part, is constructed of material having sufficient resiliency and flexibility to provide a self-biased seal against a portion of the interior surface of the more rigid part. Medical grade plastics are generally satisfactory for this purpose.

According to certain preferred embodiments, the male portion of the apparatus of this invention comprises an outer surface configured to register, in sliding seal relation, with the female portion and includes a distal end segment of enlarged diameter such that it effects a self-biased engagement with the interior surface of the female portion across an annular band of relatively small surface area. The male portion generally comprises an approximately cylindrical annulus having reduced thickness at the distal end segment. The opposite, or proximal end of the male portion and the connection end of the female portion may be cooperatively structured to form a journal bearing arrangement. The journal bearing arrangement is constructed by coupling these complementary ends in plug fit engagement, whereby to resist axial displacement of male and female portions with respect to each other.

More specifically, apparatus for openly connecting a first conduit element to a second conduit element includes complimentary female and male portions. The female portion comprises an approximately cylindrical inner surface structured for association with the first conduit element. The inner surface has a first sealing region and the female portion carries a first coupling element. The apparatus further includes a male portion comprising an approximately cylindrical outer surface structured for association with the second conduit element. The outer surface has a second sealing region in registration with the first sealing region and the male portion carries a second coupling element in registration with the first coupling element. The first and second coupling elements are constructed and arranged to effect a journal bearing connection, and the first and second sealing regions are structured to permit low friction rotation while maintaining a fluid tight seal at the interface between the inner and outer surfaces.

BRIEF DESCRIPTION OF THE DRAWINGS

In the drawings, which illustrate what is currently regarded as the best mode for carrying out the invention:

FIG. 1 is an exploded view in cross section of a valved manifold incorporating the connector of this invention;

FIG. 2 is a cross sectional view in elevation of the valved manifold of FIG. 1, illustrating the connector in assembled condition; and FIG. 3 is an enlarged view in cross section of the connector portion of FIG. 1.

DETAILED DESCRIPTION OF THE ILLUSTRATED EMBODIMENT

A swivel connector, designated generally 20, of this invention, is illustrated in association with a stop cock manifold valve, designated generally 22. The valve 22 includes a knob 24, which may be turned by finger pressure to rotate a stem 26. The stem 26 is structured with an open interior 28, defined by a continuous wall 32. When the stem 26 is installed within the manifold body 34 of the valve, as shown by FIG. 2, the open bottom 36 of the open interior 28 registers with a first manifold port 40.

The stem 26 may be rotated between a first, open position, as illustrated by FIGS. 1 and 2, wherein an opening 44 of the wall 32 registers with a second manifold port 46, and a second, closed position, in which a solid portion 48 of the wall 32 is brought into registration with the second manifold port 46. In the first position, a travel path is opened between the second manifold port 46 and a third manifold port 50 through the open interior 28 of the stem 26. In the second position, the port 46 is sealed. In both positions of the stem 26, a transverse slot 54 through the continuous wall 32 provides a flow path between the port 50 and the stem interior 28. Thus, in either position, the first manifold port 40 remains in open, fluid flow communication with the third manifold port 50 through the open bottom 36 of the stem, the stem interior 28 and the slot 54.

As best shown by FIG. 3, the connector 20 comprises a pair of cooperating female and male parts, designated generally 60 and 62, respectively. The first part 60 is embodied as a conduit structure which includes the third manifold port 50. This structure 60 constitutes a connection conduit typical of manifold devices 22 of the type illustrated, and presents an approximately cylindrical interior surface 64, constituting the female portion of the connector 20. The connection end of the female part 60 is structured as cylindrical tang 65. A cross-section of tang 65 is symmetric with respect to the central open bore axis, and is independent of said cross-section azimuth.

The male part 62 of the connector 20 has a hollow interior 66 between first 68 and second 70 open ends The first end 68 constitutes the termination of the male portion, generally 72, of the connector 20. The male portion 72 includes an outer surface 74 configured to register, in sliding seal relation, with the female portion 60 of the connector 20. This outer surface 74 is thus approximately cylindrical, and is sized appropriately for insertion within the female portion 60. A distal end segment 76 is flared to an enlarged diameter so that it effects a self-biased engagement with the interior surface 64 of the female portion 60 across an annular band of relatively small surface area. The flared segment 76 is of significantly reduced wall thickness, tapering towards the end 68.

The second open end 70 of the second part 62 of the connector 20 is structured and arranged for coupling to a system component, such as an intubation tube (not shown). A terminal segment 78 of the second end 70 may further be structured cooperatively to form a journal bearing connection, designated generally 80 (FIG. 2), with structure 82 associated with the first part 60 of the connector 20, all as best shown by FIG. 3. Terminal segment 78 and outer surface 74 are structured to form a cylindrical clevis 83. A cross-section of cylindrical clevis 83 structure that interfaces with tang 65 is symmetric with respect to the central open bore axis, and is independent of said cross-section azimuth. On assembly of swivel connector 20, clevis 83 captures tang 65 in snap fit circumferential engagement. The first 60 and second 62 parts are supported against radial displacement A—A or twist, which could interfere with smooth rotational displacement B—B of these parts with respect to each other. Specifically, in the illustrated instance, the structure 82 is formed as an annular ring which is received within a corresponding annular groove 84 comprising the terminal segment 78. These elements 82, 84 are structured and arranged to effect a firm, intimate plug fit connection which resists axial displacement C—C, but permits low resistance rotational displacement B—B, preferably over a full 360° range. As shown, the first, or female, part 60 is associated with a first conduit of a first system component (valve 22) and the second, or male, part 62 is adapted to be associated with a second conduit of a second system component (not shown).

Reference in this disclosure to details of the illustrated or other preferred embodiments is not intended to limit the scope of the appended claims, which themselves recite those features regarded as important to the invention.

What is claimed is:

1. A connector for openly connecting conduit elements, comprising:
    a first conduit element and constituting a female portion comprising an inner cylindrical surface;
    a second part associated with a second conduit element and constituting a male portion comprising an outer cylindrical surface;
    said first and second parts being structured and arranged to effect a tang and clevis connection capable of low friction rotation while maintaining a fluid tight seal at the interface between said first and second parts;
    wherein
    said first conduit element includes a connection end comprising a tang; and
    said second conduit element includes a hollow interior between:
        a first open end, constituting said male portion; and
        a second open end structured as a clevis and arranged to couple in snap-fit engagement with said connection end of said first conduit element;
    and wherein said male portion comprises:
        an outer surface configured to register, in sliding seal relation, with said female portion; and
        a distal and segment of enlarged diameter such that it effects a self-biased engagement with an inner cylindrical surface of said female portion across a relatively small surface area.

2. A connector according to claim 1, wherein said first open end of said second conduit element is flared to an increased diameter, whereby to effect a self-biased seal against an inner cylindrical surface of said first conduit element.

3. A connector according to claim 1, wherein said male portion comprises an approximately cylindrical annulus having reduced thickness at said distal end segment.

4. A connector for openly connecting conduit elements, comprising;
    a first part associated with a first conduit element and constituting a female portion comprising an inner cylindrical surface;
    a second part associated with a second conduit element and constituting a male portion comprising an outer cylindrical surface;
    said first and second parts being structured and arranged to effect a tang and clevis connection capable of low friction rotation while maintaining a fluid tight seal at the interface between said first and second parts;
    wherein:
    said first conduit element includes a connection end;
    said second conduit element includes:
        a distal end received by said first conduit element; and
        a proximal end;
    said connection end of said first conduit element and said proximal end of said second conduit element being cooperatively structured to form a journal bearing arrangement;
    and wherein said proximal end of said second conduit element is flared to an increased diameter, whereby to effect a self-biased seal against the internal surface of said first conduit element.

5. A connector for openly connecting conduit elements, comprising:
    a first part associated with a first conduit element and constituting a female portion comprising an inner cylindrical surface;
    a second part associated with a second conduit element and constituting a male portion comprising an outer cylindrical surface;
    said first and second parts being structured and arranged to effect a tang and clevis connection capable of low friction rotation while maintaining a fluid tight seal at the interface between said first and second parts;
    wherein:
    said first conduit element includes a connection end;
    said second conduit element includes:
        a distal end received by said first conduit element; and
        a proximal end;
    said connection end of said first conduit element and said proximal end of said second conduit element being cooperatively structured to form a journal bearing arrangement;
    and wherein said male portion comprises:
        an outer surface configured to register, in sliding seal relation, with said female portion; and a distal end segment of enlarged diameter such that it effects a self-biased engagement with an inner cylindrical surface of said female portion across a relatively small surface area.

6. A connector according to claim 5, wherein said male portion comprises an approximately cylindrical annulus having reduced thickness at said distal end segment.

7. A connector according to claim 5, wherein said connection end of said first conduit element and said proximal end of said second conduit element are structured and arranged to couple in plug fit engagement, whereby to resist axial displacement of said second part with respect to said first part.

8. A connector according to claim 7, wherein said first conduit element is integral with a fluid manifold structure.

9. A connector according to claim 7, wherein said proximal end of said second conduit element is further structured to couple with a tubular component.

10. A connector according to claim 7, wherein said distal end of said second conduit element is flared to an increased diameter, whereby to effect a self-biased seal against the internal surface of said first conduit member.

11. A connector according to claim 10, wherein said male portion comprises an approximately cylindrical annulus having reduced thickness at said distal end segment.

\* \* \* \* \*

UNITED STATES PATENT AND TRADEMARK OFFICE
CERTIFICATE OF CORRECTION

PATENT NO.   : 6,415,789 B1
DATED        : July 9, 2002
INVENTOR(S)  : Michael W. Freitas and Sean P. Hanson It is certified that error appears in the above-identified patent and that said Letters Patent is hereby corrected as shown below:

Column 2,
Line 19, change "multi-functional" to -- multi-function --
Line 38, change "suctioning" to -- suction --
Line 49, delete the comma after "circuitry"

Column 3,
Line 1, delete the comma after "cylindrical"
Line 40, delete the comma after "fit"
Line 43, delete the comma after "usually"
Line 59, insert a comma after "end"

Column 5,
Line 2, insert a period after "ends"
Line 51, before "a first" insert -- a first part associated with --

Column 6,
Line 4, before "segment" change "and" to -- end --
Line 17, change the semicolon after "comprising" to a colon Signed and Sealed this Twenty-seventh Day of April, 2004

JON W. DUDAS
*Acting Director of the United States Patent and Trademark Office*